United States Patent [19]
Niklason et al.

[11] Patent Number: 5,872,828
[45] Date of Patent: Feb. 16, 1999

[54] TOMOSYNTHESIS SYSTEM FOR BREAST IMAGING

[75] Inventors: Loren T. Niklason; Laura E. Niklason, both of Beverly; Daniel B. Kopans, Waban, all of Mass.

[73] Assignee: The General Hospital Corporation, Boston, Mass.

[21] Appl. No.: 898,058

[22] Filed: Jul. 22, 1997

Related U.S. Application Data

[60] Provisional application No. 60/022,276, Jul. 23, 1996.
[51] Int. Cl.$^6$ ........................................... A61B 6/02
[52] U.S. Cl. ..................................... 378/23; 378/37
[58] Field of Search ..................... 378/22, 23, 37

[56] References Cited

U.S. PATENT DOCUMENTS

| | | | |
|---|---|---|---|
| 3,746,872 | 7/1973 | Ashe et al. | 378/2 |
| 4,442,534 | 4/1984 | Haendle et al. | 378/21 |
| 4,516,252 | 5/1985 | Linde et al. | 378/23 |
| 4,853,947 | 8/1989 | Haaker et al. | 378/99 |
| 5,008,947 | 4/1991 | Yamada | 382/6 |
| 5,051,904 | 9/1991 | Griffith | 364/413.16 |
| 5,060,246 | 10/1991 | Van Der Brug et al. | 378/20 |
| 5,359,637 | 10/1994 | Webber | 378/2 |
| 5,511,106 | 4/1996 | Doebert et al. | 378/146 |
| 5,668,844 | 9/1997 | Webber | 378/2 |

*Primary Examiner*—David P. Porta
*Assistant Examiner*—David Vernon Bruce
*Attorney, Agent, or Firm*—Lappin & Kusmer LLP

[57] ABSTRACT

The invention includes both systems and methods for tomosynthesis x-ray imaging. An x-ray source is moved at various positions in an arc around an object, e.g., a breast, to illuminate a stationary digital detector (or its equivalent) placed at an image plane behind the object. A digital image data processor collects data from the detector and a motion controller moves the source around the object. As the source moves along the arc, the detector generates, for a succession of points along the arc, a corresponding succession of image data sets, each set being representative of the intensity of x-rays incident on the detector for the then current position of the source. The image data processor is responsive to the image data sets to generate an output image signal representative of the x-ray absorption of points within the object region. The processor transforms the image plane data to a form corresponding to that which would have been generated had the x-ray source moved in a linear motion in a source plane parallel to the image plane, rather than an arc. The resultant image data thus corresponds in form to that produced by a conventional linear motion, e.g., Twinning-type, system, so that conventional techniques and equipment may be used to produce a final representation of the x-ray absorption of the object region.

27 Claims, 7 Drawing Sheets

TOMOSYNTHESIS SYSTEM FOR BREAST IMAGING

RELATED APPLICATIONS

This application is a continuation-in-part of commonly-owned and copending U.S. provisional application Ser. No. 60/022,276, which was filed on Jul. 23, 1996, and which is expressly incorporated herein by reference.

BACKGROUND OF THE INVENTION

The invention is in the field of x-ray imaging and particularly relates to body section radiography, and more particularly relates to methods and systems for generating x-ray images using digital processing of raw image data.

It is well known that body section radiography techniques produce x-ray images of body parts. In early forms of x-ray imaging, x-rays were directed through the body part of interest to an x-ray detector, which provided an image based on the intensity distribution of the x-ray incident on the detector. Images produced by such techniques suffered from structured or anatomical noise which often obscured a lesion or abnormality. Structured noise is caused by normal tissue overlying or encompassing a lesion, for example. Digital processing techniques have been developed which reduce the effects of structured noise. One such technique is generally known as digital tomosynthesis. That technique utilizes digitized x-ray intensity information obtained from an array of points in a detector medium, such as radiographic film, or a digital detector. From that detected intensity data, signals are generated which are representative of the x-ray absorption of the region-to-be-imaged.

X-ray imaging has become an effective way of detecting early breast cancer. With the increasing prevalence of digital imaging, digital mammography is expected to replace film-screen mammography as the best method for the detection of breast cancer. Digital imaging is also expected to replace film-screen imaging in other areas of radiology. The introduction of digital detectors provides the opportunity to bring several methods to radiological imaging which were previously impractical. Among these methods is improved digital tomosynthesis. In mammography, implementation of this technique may result in increased survival from breast cancer, decreased mortality and a reduction in negative biopsies.

In conventional film-screen tomography methods, an x-ray source and a radiographic film-screen detector move in opposite directions, such that only features substantially in one plane of the image remain in sharp focus. Two such techniques are illustrated schematically in FIGS. 1 and 2. The Twinning technique, illustrated in FIG. 1, involves simultaneous, linear x-ray tube and detector motions, about a fulcrum in the object plane, to produce an image of the object that has only one object plane in sharp focus. The projections of features from all other planes are blurred. Using this technique, there is a range about the object plane that is considered to be "in focus". This range is referred to as the section thickness. In general, section thickness is inversely proportional to the amplitude of motion (in degrees) of the x-ray source.

The Grossman technique, illustrated in FIG. 2, is similar to the Twinning technique but involves a rotational movement of the x-ray tube and detector, again as a unit about a fulacrum point but of a fixed distance from each other. With both of these techniques, one or more exposures are necessary for each tomography plane that is imaged as well as full motion of the x-ray tube and detector through the tomographic angle.

In prior art digital tomosynthesis using the Grossman technique, multiple images are acquired as the x-ray tube is moved in an arc above the object and detector. Prior art tomosynthesis has also been accomplished using the Twinning method. By shifting and adding the images, it is possible to reconstruct any plane in the image from this limited set of images. However, such techniques have only been applied to body section imaging with detectors and sources that move with respect to the object being imaged. As a consequence, uncertainties in the position of both the source and detector contribute to image blurring.

It is an object of the invention to provide an improved tomosynthesis system and method. Another object is to provide a tomosynthesis system and method requiring low x-ray dosage. Yet another object is to provide a tomosynthesis system and method permitting generation of accurate and high resolution body section images. Still another object of the invention is to provide a tomosynthesis system having reduced mechanical complexity and increased accuracy as compared to the prior art.

SUMMARY OF THE INVENTION

The present invention is a new system and method for tomosynthesis x-ray imaging. A system in accordance with the invention includes an x-ray source, a digital detector (or its equivalent) in an image plane, a digital image data processor, and a controller. The x-ray source and detector are disposed on opposite sides of an object region disposed about an object plane parallel to the image plane. The source faces the detector so that x-rays from the source are directed toward and through the object region to the detector. The controller effects motion of the source along an arc opposite the detector. As the source moves along the arc, the detector generates for a succession of points along the arc, a corresponding succession of image data sets, each set being representative of the intensity of x-rays incident on the detector for the then current position of the source. The image data processor is responsive to the image data sets to generate an output image signal representative of the x-ray absorption within the object region. To do so, the processor transforms the image data to a form corresponding to that which would have been generated had the x-ray source moved in a linear motion in a source plane parallel to the image plane, rather than an arc. The resultant image data thus corresponds in form to that produced by a conventional linear motion, e.g., Twinning-type, system, so that conventional techniques may be used to produce a final representation of the x-ray absorption of the object region.

Thus, the invention utilizes a rotating x-ray tube and a stationary digital detector. The prior art, by way of contrast, utilizes moving detectors. One primary difference between the invention and previously described methods is the use of a stationary detector. This technique allows the reconstruction of any tomographic plane of an object region with the x-ray tube moving in an arc above the object, while a planar detector and an object region (or patient) are stationary, permitting the formation of tomographic images. The invention has the advantage that it may be easily applied to digital x-ray equipment that is already in use. Another advantage of the invention is that the detector is stationary with respect to the object being imaged, thereby eliminating one source of position uncertainty.

Another advantage of the invention is that any plane in the object that is parallel to the image plane may be reconstructed from a single set of images; whereas, in the prior art, each reconstructed plane in the object requires acquisition of a new set of images. With tomosynthesis techniques applied to mammography, a radiologist can look through a series of tomographic images and determine if a suspicious area is real or is due to the superimposition of structures. If real, tomosynthesis will present a better image of the lesion by reducing the noise from the superimposed structures. A radiologist accordingly has increased confidence in classifying lesions, which would be expected to reduce the number of biopsies of benign lesions.

BRIEF DESCRIPTION OF THE DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENT

Figure 1:
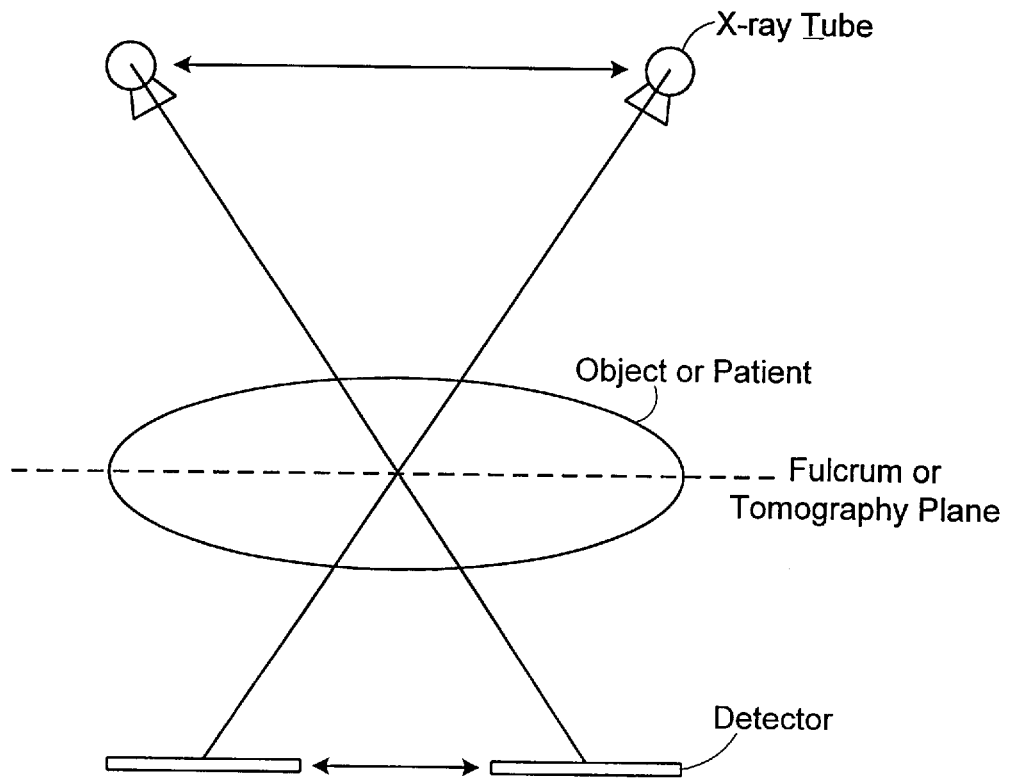
FIG. 1 shows a schematic representation of a prior art Twinning-type body section radiography system.
Figure 2:
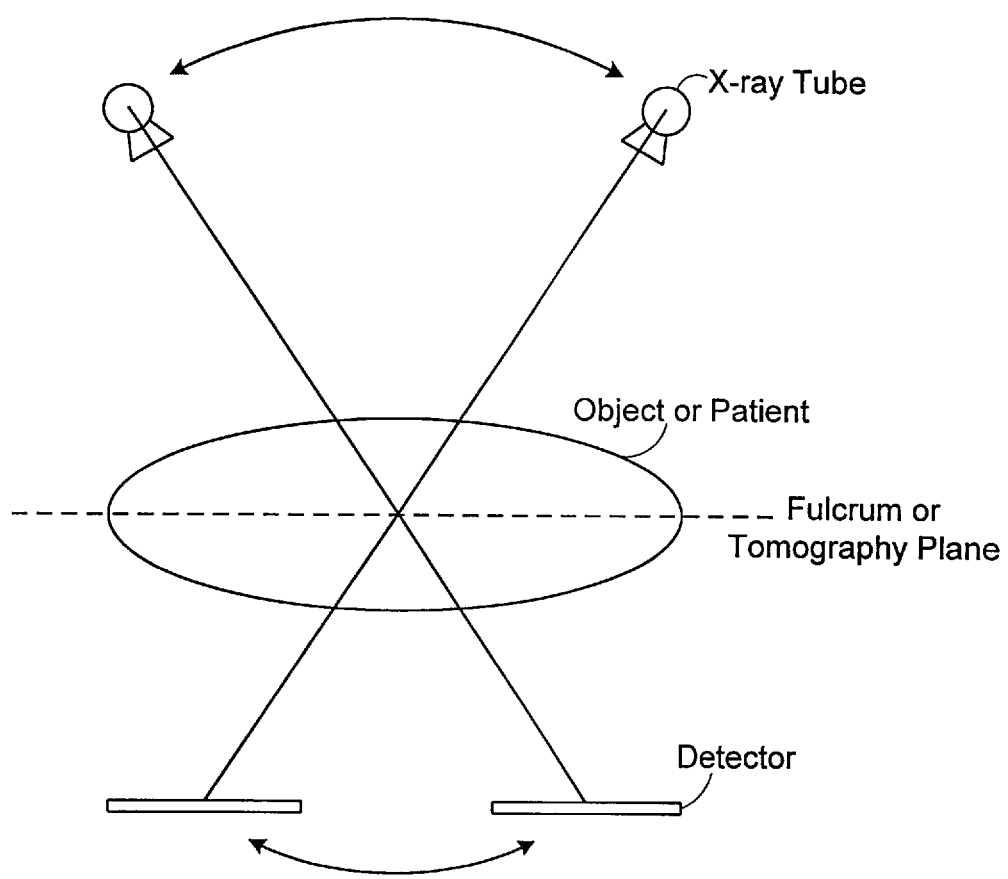
FIG. 2 shows a schematic representation of a prior art Grossman-type body section radiography system.
Figure 3:
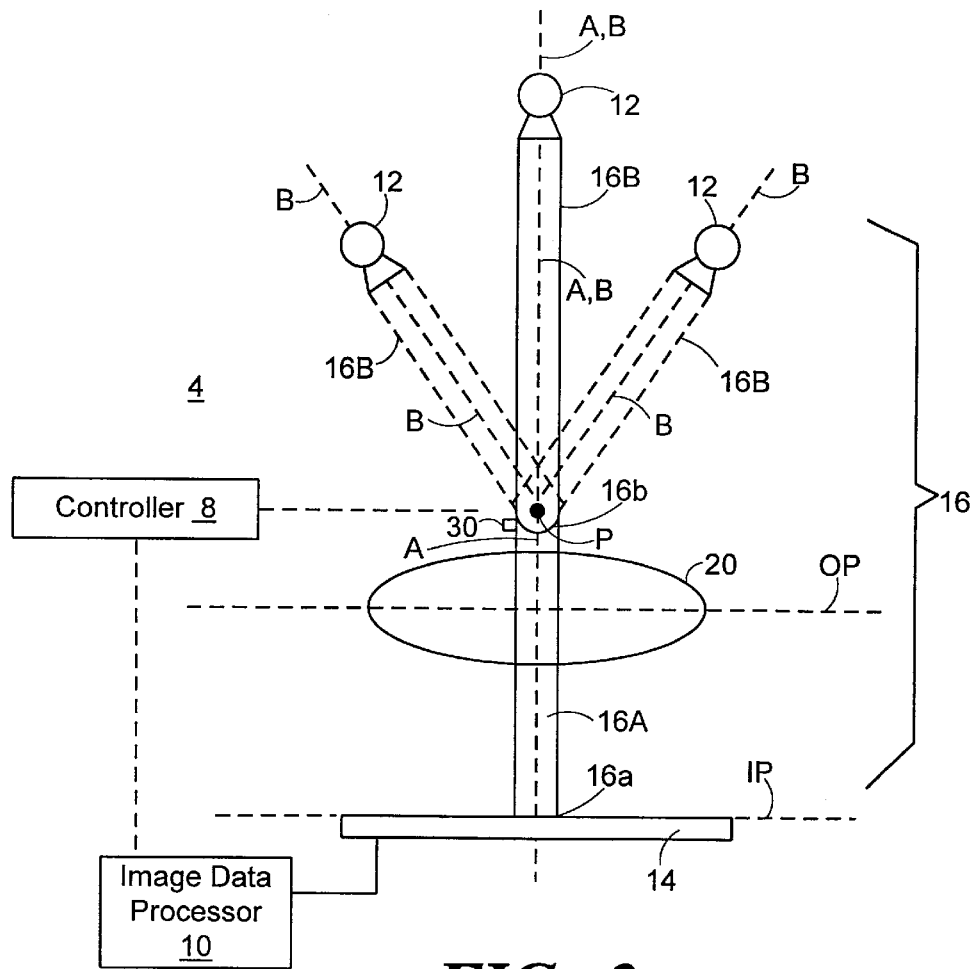
FIG. 3 shows digital tomosynthesis system constructed according to the present invention.

A system 4 embodying the invention is shown in FIG. 3. The system 4 includes a controller 8, a digital image processor 10, an x-ray source 12, and a planar digital x-ray detector 14 lying in an image plane IP. A support structure 16 supports the source 12 with respect to the detector 14, so that x-rays from the source 12 are directed toward the detector 14, as described below. An object region 20 is defined between the source 12 and the detector 14 and extending along and about an object plane OP, and in the path of x-rays passing from source 12 to the detector 14. In the illustrated embodiment, the detector 14 is a digital detector lying in an image plane IP, having a two dimensional planar array of x-ray detector elements.

In the illustrated embodiment, the support structure 16 is articulated, and includes a first portion 16A and a second portion 16B. Portion 16A extends from a proximal end 16a in a direction along an axis A, which is perpendicular to the image plane IP, to a distal end 16b and the second portion 16B extends from the distal end 16b of the first portion 16A along an axis B to the x-ray source 12. The first portion 16A and second portion 16B are pivotally coupled about an axis P at the distal end of portion 16A, where axis P is perpendicular to axis A. An actuator 30 is selectively controlled to determine the angle of portion 16B (and axis B) with respect to portion 16A (and axis A), in response to control signals from controller 8. While in the present embodiment, the axis P is between the object plane OP and the source 12, the axis P may be at or below the object plane in other embodiments. By way of example, the x-ray source 12 and support structure 16 may be a General Electric Medical Systems Model DMR Mammography System.

In the preferred embodiment, the controller 8 is a digital computer which is programmed to control the angular position of portion 16B with respect to portion 16A (and thus the position of source 12). The image data processor 10 is also preferably a digital computer programmed to the process data produced by the detector 14 in response to incident x-rays. Such a processor 10 can, in addition, function to control the emission of x-rays from source 12 such as by techniques known in the art. In other embodiments, a single programmed computer may perform the functions of both controller 8 and processor 10.

As noted above, the detector 14 in the preferred embodiment is a planar, or flat-field, detector including a two dimensional planar array of x-ray detection elements or pixels. Each of those pixel elements may include a scintillator element (which is responsive to incident x-rays to produce light photons) and a photodiode, which in turn produces a digitized signal representation of the x-ray flux incident on the scintillator element of that detector element. Other types of digital x-ray detectors may be used, flat or curved. Each of the pixel elements is interrogated by the processor 10 to provide at processor 10 digital data representative of the distribution of x-ray intensities at the image plane IP. Preferably, the pixel elements of detector 14 are part of a small geometry integrated circuit array, so that a high resolution image representation may be obtained. In alternative embodiments, either a charge coupled device (CCD) or a direct digital detector (converts x-rays directly to digital signals) can be used.

Figure 4:
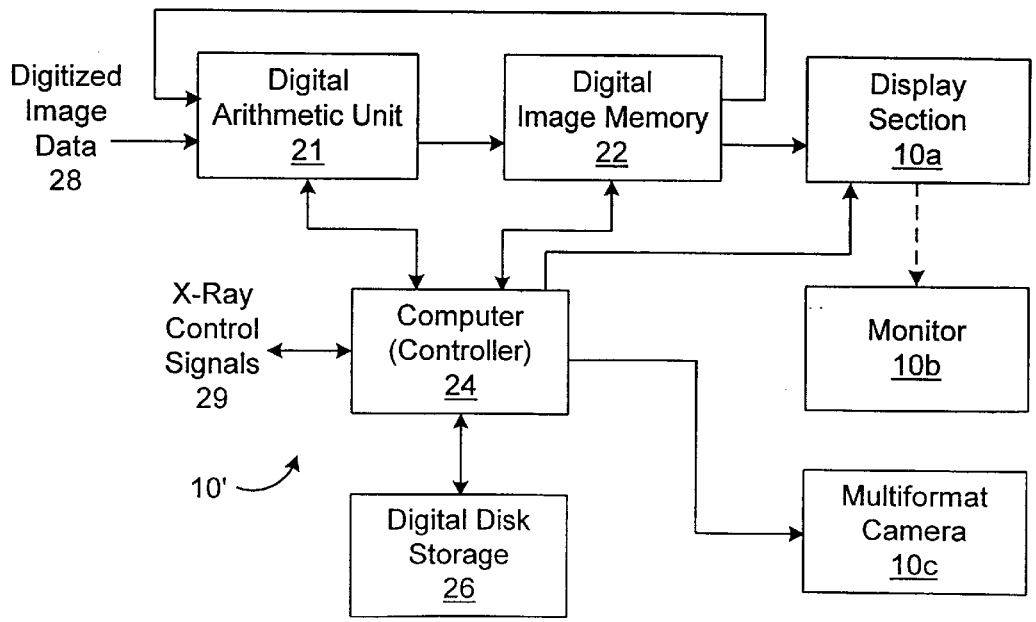
FIG. 4 shows the digital image processor of the system of FIG. 3.

The digital image processor 10 may be a conventional digital computer programmed to perform the transformations described below. FIG. 4 shows an exemplary configuration of a similar computer 10'. Specifically, the computer 10' of FIG. 4 includes a digital arithmetic unit 21, digital image memory 22, a x-ray controller 24, and digital disk storage 26. The digital arithmetic unit 21 interfaces with digital image data 28; while the controller 24 interfaces with actuator 30, FIG. 3, driving the support structure so as to move the source 12 to correct angular locations. The computer 10 can further include a display section 10a; or it can command video on a separate monitor 10b. The controller 24 can also be connected to drive other devices, such as a multiformat camera 10c; and the controller 24 can further command and control irradiation by the x-ray source such as through control signals 29.

Figure 5:
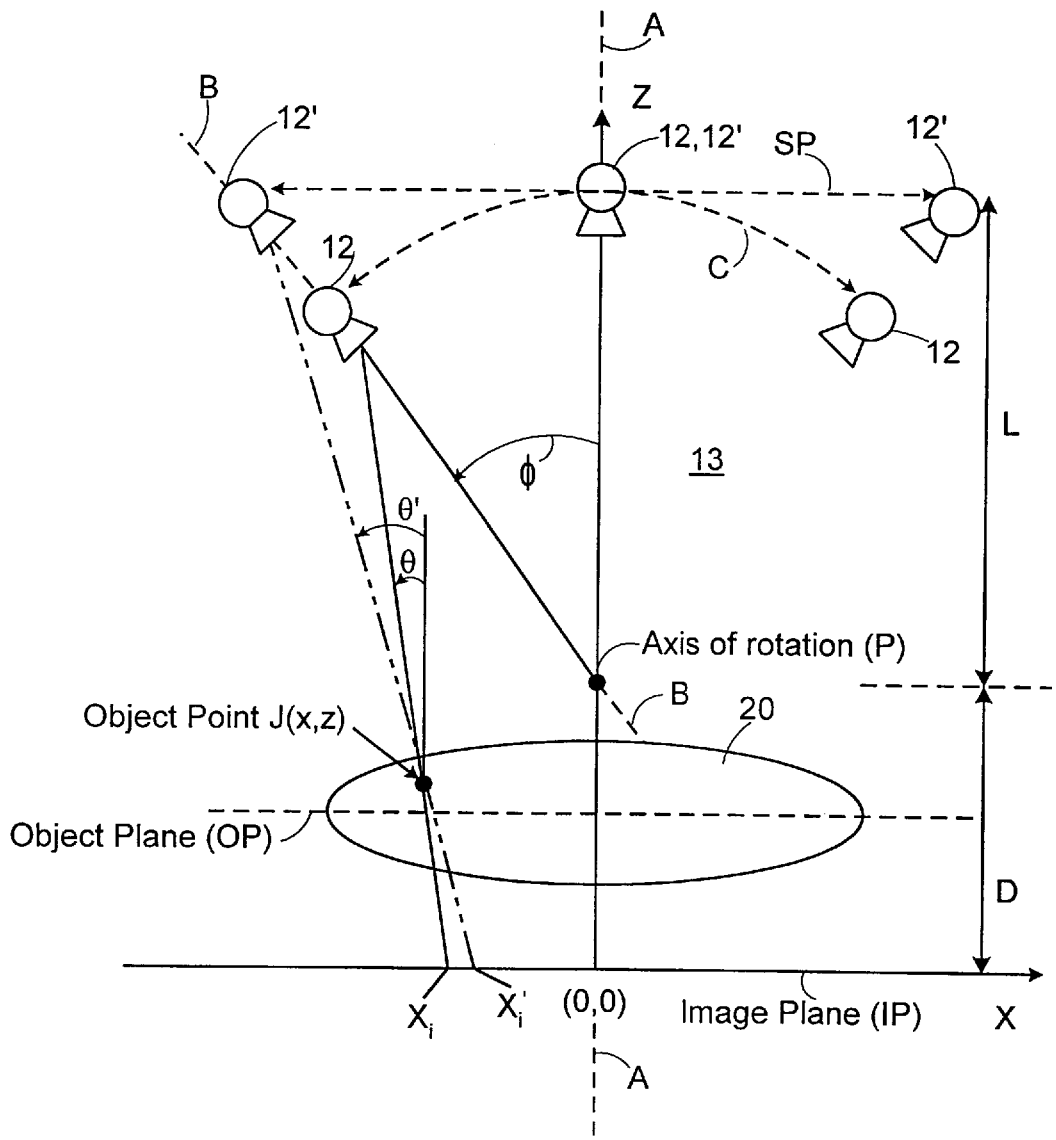
FIG. 5 shows a schematic operational representation of the system of FIG. 3.

FIG. 5 shows an operational representation of the system 10 of FIG. 4 controlling the irradiation of the object 20 and image plane IP with x-ray radiation generated by the source 12. As shown in FIG. 5, the angle $\phi$ is given by the angle of the support arm 16B, FIG. 3, relative to the perpendicular to the image plane IP. In contrast, for any given point J(x,z) in the object 20, an angle $\theta$ is defined as the angle of the x-rays intersecting the point J(x,z) relative to the perpendicular to the image plane IP. The angle $\theta$ is a function of $\phi$, x, and z, and is given by:

$$\theta(\phi, x, z) = \arctan \frac{(L\sin\phi + x)}{(L\cos\phi + D - z)} \quad (1)$$

where x and z correspond to axes in the plane of source rotation, and where L and D are defined in FIG. 5. From this angle $\theta$, the point $x_i$ is the projection of the object point J(x,z) onto the image plane IP:

$$x_i(\phi, x, z) = x + \frac{z(L\sin\phi + x)}{(L\cos\phi + D - z)} \quad (2)$$

$x_i(\phi,x,z)$ is thus the image point formed by x-rays emitted from an x-ray tube that is moved by rotation along arc C about the axis P. With this type of motion, the perpendicular distance of the focal spot from the image plane depends on the angle $\phi$. This is in contrast to images that are formed based on the Twinning principle, where the focal spot moves in a horizontal source plane SP parallel to the image plane IP. Thus, points in the object are magnified by a function not only of the position, but also of the angle $\phi$:

$$M(\phi, z) = \frac{(L\cos\phi + D)}{(L\cos\phi + D - z)} \quad (3)$$

With rotation of the x-ray tube along arc C, the magnification of object points varies with $\phi$. Therefore, a tomosynthetic reconstruction of an object plane defined by z=(a constant) cannot be accomplished by simply shifting the image points by a function of z, as may be done with images formed by the Twinning principle. In accordance with the invention, the image that is formed by rotation of the tube is transformed to construct a new image that approximates that which would have been formed if the focal spot were moved in a source plane SP parallel to the image plane IP i.e. along broken line SP as shown in FIG. 5. This new image data is utilized to reconstruct a tomographic plane in the object by a simple shifting and addition of image data sets.

More particularly, if the x-ray source 12 were rotated by an angle $\phi$, but constrained to remain in the horizontal plane a distance (L+D) from the image—such as shown by source positions 12'—then the angle of the x-rays intersecting an object point would be given by:

$$\theta'(\phi, x, z) = \arctan\frac{(L\tan\phi + x)}{(L + D - z)} \quad (4)$$

From Eq. 4, the image point $x_i'$, which would be the projection of the object point J(x,z) from SP onto the image plane IP, is given by:

$$x_i'(\phi, x, z) = x + \frac{z(L\tan\phi + x)}{(L + D - z)} \quad (5)$$

In accordance with the invention, the x-ray gantry thus produces images with image points as defined by Eq. 2. For every $x_i$ in the image, a known value of $\phi$ is used with a selected z to determine an object point x from Eq. 2. The values of $\phi$, x, and z are then applied to Eq. 5 to determine a value for $x_i'$ in the new image. The set of new images produced are then utilized to reconstruct a tomographic plane OP at z by a simple linear shifting process analogous to the Twinning method.

The technique for construction of a new set of images for each desired tomographic plane results in a small distortion of image information for structures outside the plane OP. This is because the x-ray paths through the object 20 that occur with rotation of the focal spot about an axis P are slightly different from those that occur when the focal spot is moved within a horizontal plane. The magnitude of the distortion increases with the distance from the reconstructed plane, and also increases with the distance from the central axis of the image, i.e., where x=0. The distortion for all points that lie exactly on the reconstructed plane OP is zero. For purposes of illustration, assume an imaging system of the invention is constructed with values of L=44 cm, D=22 cm, $\phi$=15°, and with a reconstructed plane z=4 cm above the image plane. For a reconstructed plane at x=10 cm, the maximal distortion for an object positioned 5 cm above the reconstructed is approximately 195 microns. Since the linear tomographic shift for this imaging geometry is approximately 7,606 microns, this distortion corresponds 2.5% of the tomographic shift. Thus, the magnitude of the distortion caused by creation of the new image is small compared to the amount of linear shift utilized for the tomographic reconstruction. For this reason, distortion produced by the invention does not have a significant effect on the tomographic image quality.

The invention is thus particularly useful in imaging breasts utilizing a full field digital mammography system. Tomosynthesis in this manner allows reconstruction of "in-focus" tomographic planes at any level in the breast. The radiation dose is low and comparable to a single-view conventional mammogram. Preliminary results indicate that the visibility of masses is increased with tomosynthesis according to the invention. Tomosynthesis of the invention further has the potential to improve the specificity of mammography with improved lesion margin visibility and to improve early breast cancer detection, especially for women with radiographically dense breasts.

Figure 6:
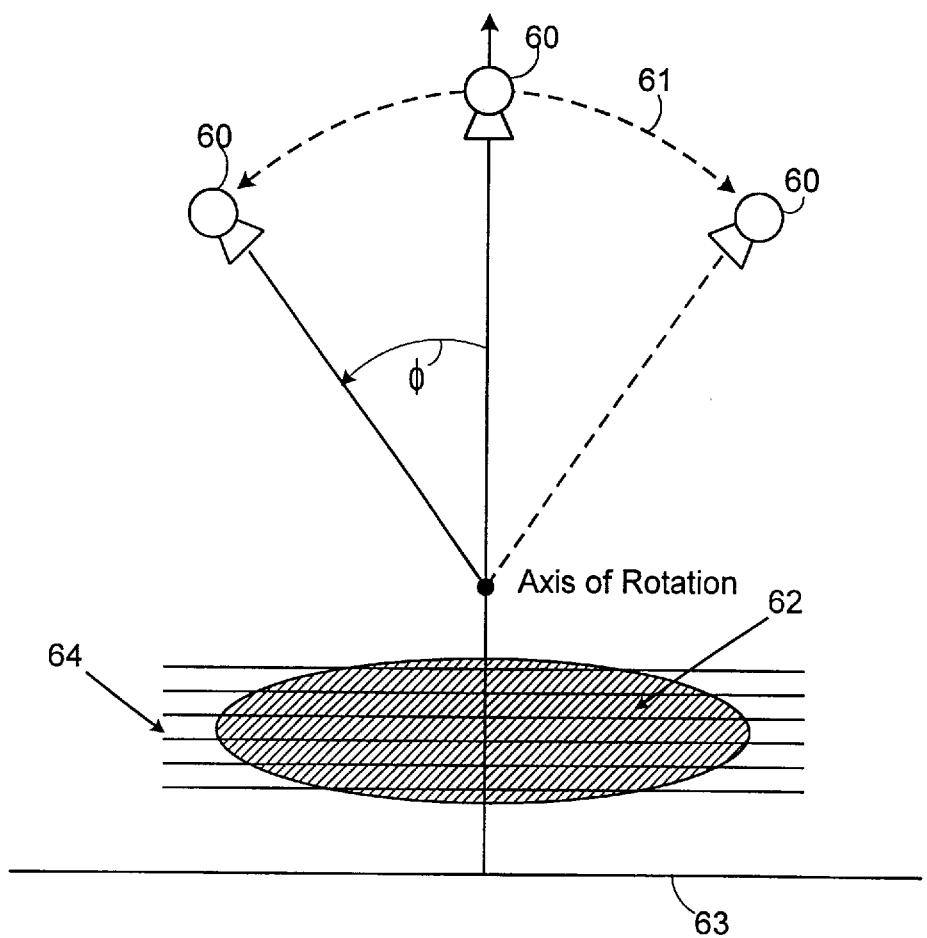
FIG. 6 illustrates operational aspects of the invention so as to acquire tomosynthesis planes.

In particular, the invention provides advantages which allow the radiologist to see through "structured noise" of normal breast tissue so as to improve detection and characterization of the breast cancer. In conventional film-screen tomography, the x-ray source and the film-screen detector move in opposite directions, so that only features in one plane of the image remain in sharp focus. In the tomosynthesis methods of the invention, such as shown in FIG. 6, multiple images are acquired as the x-ray tube, i.e., the "source" 60, is moved in an arc 61 above the stationary breast 62 and detector 63. The images obtained at each angle $\phi$ by the detector 63 are of low radiation dose, with the total radiation dose for all of the images being equivalent to, or slightly higher than, the dose used for a standard single view mammogram. By shifting and adding the digital images, and after transformation of the images by equation (5) above, it is possible to reconstruct any plane 64 in the breast that is parallel to the detector 63, i.e., at any selected value for "z" in the breast. The technique of the invention thus provides a series of images of the entire breast 62, with each image displaying only one plane 64 of the breast in sharp focus.

Note, with reference to FIG. 5, that the source 12 spans an arc C defined by angle $\phi$ and within a plane 13 formed by axes X and Z. Thus, the plane 13 preferably extends through approximately the centers of the object 20 and the detector or image plane IP.

The invention preferably makes use of full-field flat digital detectors that exhibit rapid readout times. Such detectors make tomosynthesis imaging of the breast practical in clinical settings because of low noise, large flat surface area with minimal image distortion, and rapid image readout times.

Figure 7:
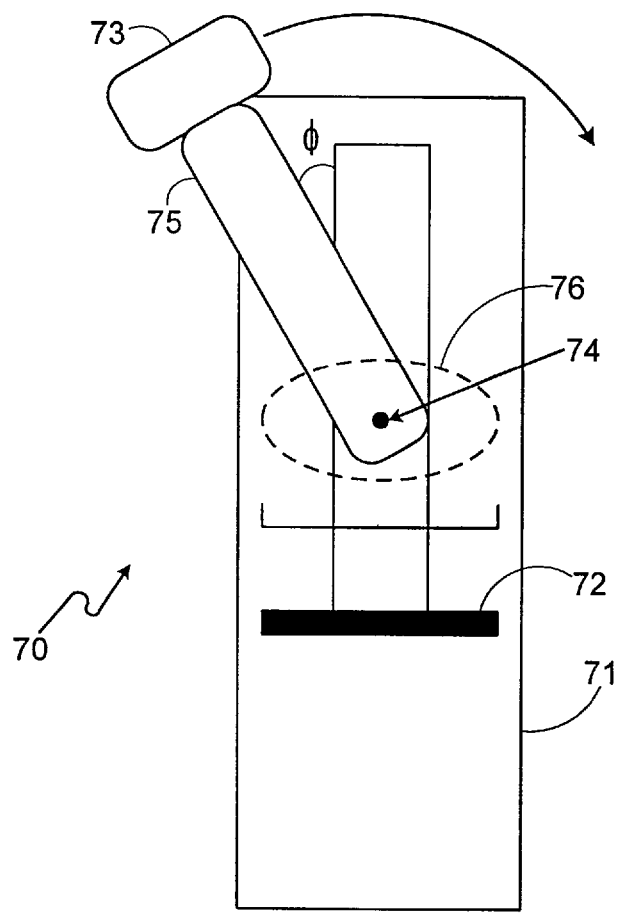
FIG. 7 illustrates one mechanical configuration, according to the invention, for rotating an x-ray tube about an axis of rotation and relative to a stationary detector.

The invention can take advantage and utilize existing hardware in forming, for example, a mammography system according to the invention. FIG. 7 illustrates one system 70, constructed according to the invention, which utilizes a General Electric model DMR mammography gantry 71 with a full-field digital image receptor 72. The system allows imaging at any angle $\phi$ up to ±27 degrees from the perpendicular to the detector 72. As shown in FIG. 7, the x-ray source 73 pivots from an arm 75 and about a point 74 above the detector 72. The x-ray source 73 is stationary during the exposure and then is moved to the next position before obtaining the next image. Preferably, the motion of the x-ray source is motorized and controlled by a computer; however, the source can also be moved manually.

In one embodiment of the invention, the digital detector 72, FIG. 7, is composed of a Cesium Iodide (CsI) phosphor on an amorphous-silicon transistor/photodiode array by General Electric Corporation. This detector 72 has a pixel pitch of one hundred microns and the image readout time is three hundred milliseconds.

The invention preferably incorporates an actuator or control mechanism 76 to determine and acquire a selected angle φ of the arm 75. By way of example, the angle φ can be determined with a Lucas Control System Products (Hampton, Va.) high resolution precision inclinometer (model 02538-01) with a range of ±20 degrees and an accuracy of ±0.1 degrees from zero to ten degrees, and ±1% for ten to twenty degrees.

Figure 8:
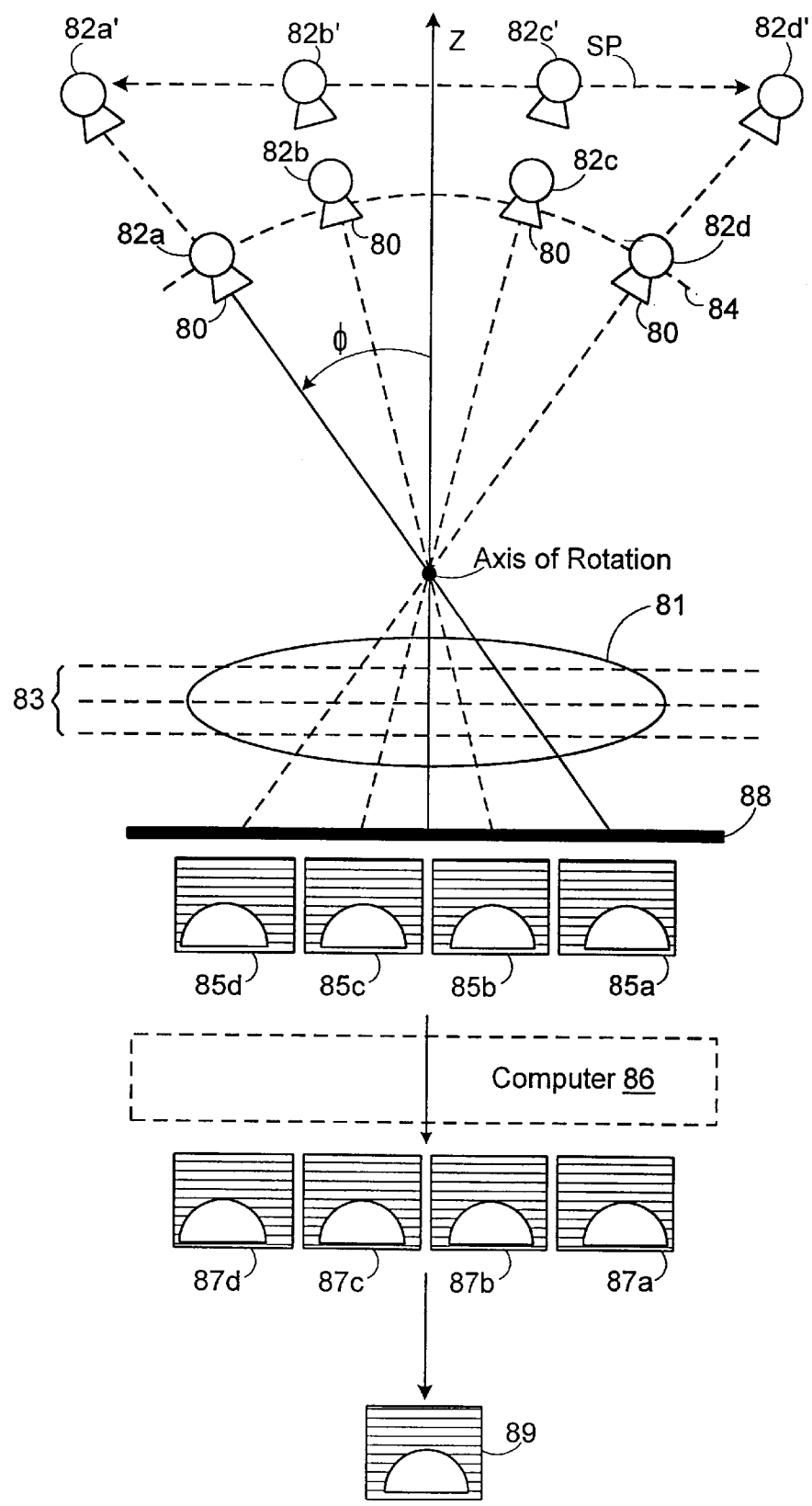
FIG. 8 shows reconstruction process and image acquisition in accord with the invention.

FIG. 8 illustrates the acquisition of tomosynthesis projection images, according to the invention, from discrete x-ray source positions 82a–d along an arc 84 above the target breast 81. For clarity of illustration, only four x-ray source positions 82 are shown. However, those skilled in the art should appreciate that the source 80 can be moved to any number of x-ray source positions 82 selectively. Tomosynthesis images of any plane 83 in the breast 81 are then reconstructed using the methods described herein. In particular, the projection images 85a–d from the x-ray source positions 82a–d, respectfully, are transformed by a digital processor 86 to simulate images 87a–8d that would be obtained from an x-ray source located at positions 82a'–82d'. In these transformations, the detector 88 does not move; rather, detector motion is simulated by shifting the images 87 in the computer 86. The transformation and shifting algorithms are repeated, if desired, to reconstruct the tomography image 89 for any plane 83 along the Z axis above the detector 88. The mathematical reconstruction algorithms to obtain the image 89 were previously described.

Typical images obtained through a system of the invention can be made at 26–30 kVp, 10–40 mAs per view, and six to ten views between about ±20 degrees (i.e., range of the angle φ). The summed mean glandular radiation dosage for the tomosynthesis images can be, for example, larger than or less than that of the conventional film-screen image.

Tomosynthesis images of the invention can be reconstructed, for example, on a Sun Microsystems Sparc 20 workstation. After initial images are acquired for each angle φ, reconstructed tomography images at 1.5 to 3 mm spacing can be made to acquire in-focus images of entire breasts.

In the preferred embodiment of the invention, images are acquired at discrete tube positions, rather than continuously as the tube moved such as in the prior art. Consequently, the blurring of structures is not a smooth blurring typical of continuous image acquisition. For example, if nine images are used in the tomosynthesis data set, objects above or below the in-focus plane will be displayed as nine separate objects in the reconstructed image. Each object will have approximately one ninth the contrast of the original object. For high contrast objects such as a large calcification, nine images of the calcification may be visible. Image structures outside of the in-focus plane are essentially repeated in the direction of x-ray source motion. High frequency information is retained, although the contrast of out-of-plane structures in greatly reduced.

The reconstructed image can be improved further. For example, self-masking tomosynthesis reduces low frequency information in the direction of the x-ray source motion. Because of discrete sampling, other image processing methods can also be used to reduce the contribution of out-of-focus structures such as from planes above or below the in-focus plane. By way of example, one suitable technique identifies the plane of an out-of-focus structure such as a dense calcification and computes its contribution to all other planes. The image of the structure is then removed from all planes except the plane containing the structure "in-focus".

In accord with the invention, there are several potential uses of tomosynthesis for breast imaging. First, tomosynthesis may prove to be a valuable screening tool for women with radiographically dense breasts. The ability to "see into the middle of the breast" by blurring the superimposed structures can permit significant improvements in the sensitivity of mammography screening in the early detection of breast cancer. Tomosynthesis according to the invention may also have the potential to detect cancers in dense breasts or multi focal cancers at a small fraction of the cost of magnetic resonance imaging. Tomosynthesis of the invention may also be used for problem solving or diagnostic breast imaging. Current mammographic techniques have poor specificity, since 70–90% of all breast biopsies are negative, whereas tomosynthesis of the invention may provide the radiologist with an improved image of a potential lesion. The invention can also provide advantages in providing a radiologist with greater confidence in lesion classification and in decreasing the number of benign biopsies. The invention further facilitates performing the entire diagnostic evaluation of a lesion with diagnostic examinations, saving time and reducing patient radiation exposure.

Other advantages are also realized by the invention. For example, tomosynthesis according to the invention will provide three dimensional information concerning the dimensions of a lesion, whether micro calcifications are associated with a mass, and how they are distributed. The three dimensional distribution of calcifications is thought to be a useful indicator in discriminating benign versus malignant lesions and thus may also have a positive impact on clinical patient management. Further, the tomosynthesis methods of the invention are adaptable to current mammography systems with minor modifications. By way of example, the image acquisition geometry of the invention has several advantages: 1) there are no moving parts near the breast or abdomen, 2) existing mammography machines may be easily altered to allow this type of motion, since many already provide the ability for the tube to move in an arc above the breast, and 3) a unit modified to do tomosynthesis imaging will still be completely useable for routine breast imaging, thereby eliminating the need for a dedicated tomosynthesis system. Motorized motion of the x-ray tube allows for the acquisition of all of the tomosynthesis images in approximately three to five seconds, a time which is sufficiently rapid to make the system clinically applicable since these exposure times are similar to magnification views with current systems.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

In view of the foregoing, what is claimed is:

1. System for performing digital tomosynthesis on an object region, comprising: a stationary x-ray detector for detecting x-ray radiation transmitted through the object region and for producing image data representative of the intensity of the radiation; a moveable x-ray source for generating the x-ray radiation; a motion controller for moving the x-ray source to a plurality of positions defining an arc about the region; and a data processor for determining x-ray absorption points within the region based upon an image data set having image data corresponding to each of the positions.

2. System according to claim 1, wherein the data processor comprises means for generating an image signal representing the region as a spatial map of the points, each point defining absorptivity of x-ray radiation within the region.

3. System according to claim 1, wherein the arc spans a plane and has an axis of rotation on a line in the plane that is perpendicular to the detector and that extends through approximately the center of the detector.

4. System according to claim 3, wherein the object region is disposed about an object plane, the data processor further comprising means for transforming the image data to a form representative of the expected intensity of x-ray radiation generated by the source at an offset position defined by the intersection between (a) a line in the plane of the arc that is substantially parallel to the object plane, and (b) a line in the plane of the arc defined by the axis of rotation and by one of the positions corresponding to the image data.

5. System according to claim 3, wherein the intersection between the axis of rotation and the plane of the arc defines a center of rotation that is between the source and the detector.

6. System according to claim 1, wherein the line that is substantially parallel to the object plane is also tangential to the arc.

7. System according to claim 1, wherein the source comprises an x-ray tube.

8. System according to claim 1, wherein the detector comprises an array of x-ray detector elements and wherein the image data comprises a plurality of intensity data values, each of the values corresponding to x-ray radiation detected by each of the elements.

9. System according to claim 1, wherein the detector comprises a two-dimensional array of detector elements and wherein the image data comprises a plurality of intensity data values, each of the values corresponding to each of the elements.

10. System according to claim 1, wherein the controller comprises a first rigid support structure having a proximal end located at about a center of rotation of the arc and a distal end for rigidly supporting the detector.

11. System according to claim 10, wherein the controller comprises a second rigid support structure having a first end pivotably connected to the proximal end of the first support structure at the center of rotation and having a second end for supporting the source at a fixed distance from the center of rotation, wherein the source is rotatable about the center of rotation and along the arc.

12. System according to claim 11, wherein the source is constructed and arranged to irradiate x-ray radiation substantially aligned with the second support structure and towards the center of rotation.

13. System according to claim 11, further comprising an actuator, responsive to angular control signals from the controller, for moving the source to an angle formed between the first and second support structures, the angle being indicative of one of the positions.

14. System according to claim 11, wherein the controller comprises means for determining an angle between the first and second support structures.

15. System according to claim 1, wherein the controller comprises means for determining an angle formed between (a) a line perpendicular to the detector and extending through a center of rotation of the arc and (b) a line defined by the center of rotation and a location of the source on the arc.

16. System according to claim 1, wherein the controller comprises a computer having means for selectively controlling the position of the source along the arc.

17. System according to claim 1, wherein the data processor comprises a computer.

18. System according to claim 17, wherein the computer further includes means for controlling the motion controller to move the source selectively along the arc.

19. System according to claim 17, wherein the source is responsive to the computer to turn the source on and off selectively.

20. System according to claim 1, wherein the detector comprises a plurality of scintillator elements and associated photodetectors, each photodetector producing a digitized signal representing x-ray flux intensity for one of the elements.

21. System according to claim 1, wherein the detector comprises an integrated circuit array.

22. System according to claim 1, further comprising an x-ray gantry having (a) a first arm for pivotably supporting the source about the center of rotation and (b) a second arm for rigidly supporting the detector relative to the center of rotation.

23. System according to claim 22, further comprising a computer for controlling the gantry so as to move the source to selected positions corresponding to an angle formed between the first and second arms.

24. System according to claim 1, wherein the detector comprises a cesium iodide phosphor on an amorphous silicon photodiode array.

25. A method for tomosynthesis x-ray imaging of an object, comprising the steps of:

(A) irradiating the object, with x-ray radiation, from a series of positions defining an arc about the region, the arc spanning a plane intersecting the object and having an axis of rotation on a line in the plane and perpendicular to the array, (B) detecting the radiation transmitted through the object with a stationary detector array and storing image data for each of the positions, the image data being representative of x-ray intensity values, and (C) determining x-ray absorption points within the object based upon an image data set having image data corresponding to each of the positions.

26. A method according to claim 25, further comprising the step of transforming the image data, for each of the positions, to a form representative of the expected intensity of the radiation generated at an offset position defined by the intersection between (a) a line in the plane that is substantially parallel to the array, and (b) a line in the plane defined by the axis of rotation and by one of the positions corresponding to the image data.

27. In a mammography system of the type having an x-ray source that rotates in an arc about the breast to irradiate the breast from different positions on the arc, the arc having an axis of rotation and spanning a plane that intersects the breast, the improvement comprising:

a stationary x-ray detector for detecting x-ray radiation transmitted through the breast and for producing image data representative of the intensity of the radiation; and a data processor for determining x-ray absorption points within the breast based upon an image data set having image data corresponding to positions along the arc, the processor having means for transforming the image data, at each of the positions, to a form representative of the expected intensity of x-ray radiation generated by the source at an offset position defined by the intersection between (a) a line in the plane that is substantially parallel to the detector, and (b) a line in the plane defined by the axis of rotation and by one of the positions corresponding to the image data.

* * * * *